United States Patent [19]
Seltzer et al.

[11] Patent Number: 5,596,405
[45] Date of Patent: Jan. 21, 1997

[54] METHOD OF AND APPARATUS FOR THE CONTINUOUS EMISSIONS MONITORING OF TOXIC AIRBORNE METALS

[75] Inventors: Michael D. Seltzer, Ridgecrest, Calif.; Robert B. Green, Richland, Wash.

[73] Assignee: The United States of America as represented by the Secretary of the Navy, Washington, D.C.

[21] Appl. No.: 540,602

[22] Filed: Oct. 3, 1995

[51] Int. Cl.$^6$ .......................... G01J 3/443; G01N 21/73
[52] U.S. Cl. .......................... 356/316; 356/36; 356/243
[58] Field of Search .......................... 356/36, 316, 243

[56] References Cited

U.S. PATENT DOCUMENTS 5,315,369  5/1994  Zadgorska et al. .................... 356/316

Primary Examiner—F. L. Evans
Attorney, Agent, or Firm—Stephen J. Church; Melvin J. Sliwka; John L. Forrest, Jr.

[57] ABSTRACT

A portable apparatus for continuous real-time measurement of airborne metals, comprising an isokinetic sampler, a sample line, a sampling interface device, a pump, and an inductively coupled plasma atomic emission spectrometry (ICP-AES). A method for measurement of airborne metals by use of such an apparatus is also described, in which the sampling interface device accommodates the high, continuous sample collection flow-rates necessary for isokinetic sampling while at the same time permits sample air to be introduced into the plasma at preferred moderate flow-rates. A method for field standardization of the ICP-AES is also described whereby a relationship between aqueous solutions of metals and their aerosol counterparts is established, thus later allowing the field use of the aqueous metal solutions to simulate a particular range of airborne metal concentrations.

10 Claims, 5 Drawing Sheets

METHOD OF AND APPARATUS FOR THE CONTINUOUS EMISSIONS MONITORING OF TOXIC AIRBORNE METALS

BACKGROUND OF THE INVENTION

1. Field of the Invention

The present invention generally relates to a method of and apparatus for continuous, near real-time measurement of airborne metals emitted into the atmosphere by furnaces, incinerators, boilers, and other combustors and detected by inductively coupled plasma atomic emission spectrometry (ICP-AES). This apparatus can provide emission data in the expeditious time frame required to facilitate pollution control efforts. The invention specifically relates to the introduction of air samples to an ICP-AES apparatus whereby sample loss is minimized, a sampling interface is employed so that isokinetic sampling of the air sample from the combustor can be utilized and a computer is coupled to the ICP-AES apparatus which provides an alarm or feedback signal if a maximum emissions level is reached.

2. Prior Art

Present and future regulatory restrictions on the rates and composition of hazardous air pollutant (HAP) emissions are creating a need for faster, more sensitive, and more reliable methods of monitoring these emissions. The traditional methods for monitoring airborne metals, EPA Methods 5 and 29, are both labor-intensive and time-consuming.

Determination of airborne metals presently requires a sample collection step, typically on a cellulose or glass fiber filter. The air to be tested is sampled for many hours. The filter is then transported to a laboratory where the filter media is chemically digested to recover and dissolve any captured metal elements. The digest is analyzed by an appropriate spectroanalytical technique such as atomic absorption spectrometry. One problem associated with this method is that the sensitivity is directly dependent on the duration of the sample collection process. Sample air has to be collected over a long time to meet the low detection levels required. This approach is insensitive to transient events since it involves time-averaging over a long time. Since the analytical result is available only after the fact, it has limited value in terms of process control aimed at pollution prevention.

There have been several approaches to continuous emissions monitors for measuring HAP metal concentrations such as: X-ray fluorescence spectrometry, laser assisted spark spectrometry, and ICP-AES. For many approaches speed and sensitivity are mutually exclusive goals. With X-ray fluorescence the sample collection process is relatively slow. X-ray fluorescence also requires expensive equipment which is designed to measure only for specific pollutants. In the laser assisted spark spectrometry technique, the sensitivity is limited for several important HAP metals. Another disadvantage of the laser assisted spark spectroscopy is it is not as accurate as the ICP-AES apparatus. The laser pulses and takes minute, pinpoint measurements of the airborne metals, whereas the ICP-AES apparatus measures larger, more representative volumes of air. Also, a reliable standardization scheme for the laser assisted spark spectroscopy has not been shown.

An apparatus for in situ detection of airborne metal aerosols was reported that involved the suction of ambient air through a plasma sustained in a quartz confinement tube mounted inside a helical induction coil. Aqueous standards were used for standardization, allowing for such factors as nebulizer efficiency and atmospheric water vapor content. A major disadvantage of the sample introduction approach used here is that the entrained analyte is dispersed throughout the plasma rather than concentrated in the central, or analytical region where excitation processes are optimum. Thus, the analyzer is insensitive to lower concentrations of airborne metals.

A method for detection and measurement of the metallic aerosol concentrations in atmospheric air was disclosed which involved channeling the sample through direct suction to the plasma. A disadvantage with this method is that the sample air flow has to be physically restricted, since the suction would cause the sample air to flow through the plasma too fast for an accurate spectroscopy reading of the emitted metal aerosols in the sample air. For standardization of the ICP-AES apparatus a relationship between the aqueous solutions of certain metals and their aerosol equivalents was also disclosed. A disadvantage with this standardization method is that it was based on an inefficient nebulization process. The amount of metal in an aerosol is calculated based on this "known" inefficiency.

Instrumentation capable of real-time and accurate detection of airborne metals emitted from industrial combustors and incinerators is not available presently. There has been interest in recent years in the development of instrumentation and methodology to permit direct sampling and analysis of airborne metals. This instrumentation and methodology would allow continuous, real-time monitoring of these metals. Real-time monitoring has an advantage in that results are available instantaneously and can be of significant value for controlling pollution in the time frame that it is occurring. Real-time data can be used as feedback in a process control loop designed to facilitate optimum operation of an incinerator or other combustor while promoting operation that meets environmental regulations.

SUMMARY OF THE INVENTION

The present invention concerns the modification of a commercially available inductively coupled plasma to allow the introduction of a sample air stream. The ICP-AES apparatus offers the best combination of speed and sensitivity for continuous emissions monitoring of hazardous air pollutant (HAP) metals. The ICP-AES apparatus was designed for the elemental analysis of liquid samples or chemically digested solid samples. The present invention was designed specifically for monitoring and measuring airborne metal concentrations. An advancement offered by the present invention is that modifications of the ICP-AES apparatus included the unique feature of a sampling interface device to accommodate high, continuous sample collection flow-rates from the incinerator or combustor while simultaneously allowing sample air to be introduced into the plasma of the ICP-AES at moderate flow-rates, necessary for accurate identification and quantification of a wide range of HAP metals. This process of sampling at the natural high-flow rate is called isokinetic sampling. A computer is coupled to the ICP-AES apparatus and sampling interface device to control the opening and closing of the solenoid valves. The computer stores and analyzes the emissions signals and determines the relationship between the aqueous equivalent metal concentrations and the aerosol metal concentrations, thus allowing field standardization of the ICP-AES apparatus. The computer also analyzes the absorption/emissions of the air samples and can determine a characteristic pattern for tested metal pollutants. Thus, the computer determines which metal pollutants are in the air sample as well as metal pollutant concentration. The computer can provide a feedback control signal or an alarm if a maximum concentration for a given metal pollutant exceeds a preprogrammed level.

Accordingly, it is an object of the present invention to provide an ICP-AES apparatus for analyzing air samples that is highly specific, versatile, and inexpensive.

Another object of the present invention is to provide a portable, continuous, real-time monitoring system for use in an ICP-AES apparatus in detecting airborne metals emitted by incinerators and other combustion creators, thus providing a nearly instantaneous indication of present regulatory compliance status.

A further object of the invention is to provide a sampling interface device for use in an ICP-AES apparatus which will maintain the good sensitivity and high efficiency of the ICP-AES apparatus while permitting isokinetic sampling of the effluent from the combustor.

A still further object of the invention is to provide a method for field standardization of the ICP-AES apparatus whereby aqueous solutions of metals are used at appropriate concentrations that simulate a particular range of airborne metal concentrations.

A still further object of the invention is to provide feedback signals during the continuous emissions monitoring, thus providing a monitoring system sensitive to transient events.

These and other objects, features and advantages of the present invention will become apparent to those of skill in the art from a thorough consideration of the detailed description, taken in conjunction with the accompanying drawings, which follows.

DETAILED DESCRIPTION OF THE INVENTION

Figure 1:
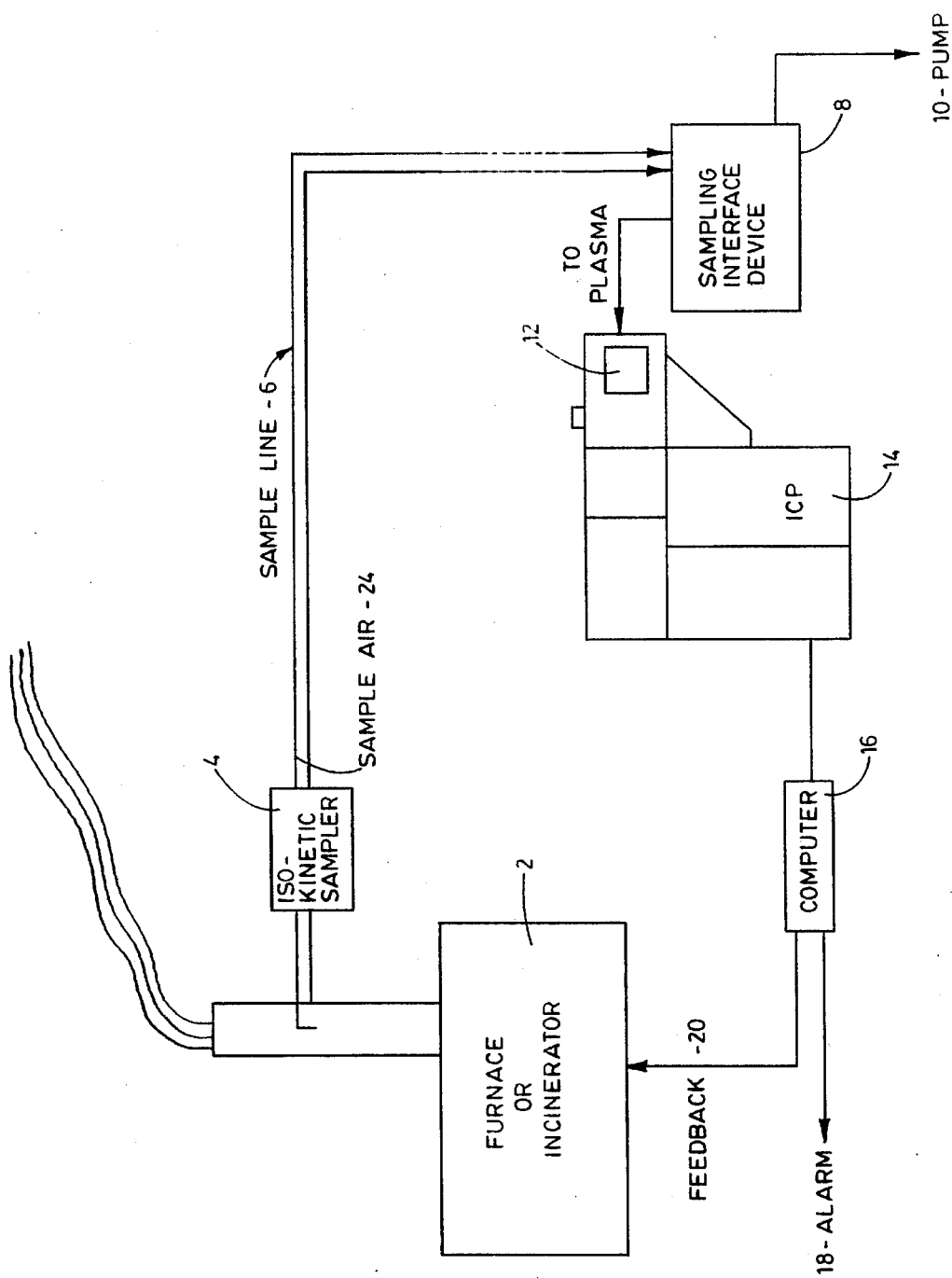
FIG. 1 illustrates a schematic diagram of the method of sample collection and transport to continuous emissions monitor.

FIG. 1 illustrates the method of sample collection. An automated isokinetic sampling system (isokinetic sampler) 4, having the conventional sampling nozzle, flow sensors and regulated pump can be used to collect sample air 24 containing pollutant metals from the incinerator 2 at the velocity the sample air 24 is being emitted. The isokinetic sampler 4 is commercially available, for example, a Kurz isokinetic sampler was utilized. The sample air 24 is then transported through a sample line 6, which is preferably heated, through the sampling interface device 8 by means of a pump 10. Any heating means can be used, for example a Technical Heaters, Inc. sample line, containing an electrical heating element was used. In a preferred embodiment of the invention the sample line 6 transporting the sample air 24 to the ICP-AES apparatus 14 should be as short as possible, in order to avoid the metal pollutants in the sample air 24 from being lost in the sample line 6.

The optimum rate of sample air introduction into the plasma 12 of the ICP-AES apparatus 14 is between about 0.5 and 1.0 L min$^{-1}$, which is also the optimum carrier gas flow-rate during conventional operation during the testing of liquid samples. Sample air velocity coming from an incinerator 2 or other industrial combustor is often much higher than the optimum rate of sample air 24 introduction, for example 10–20 l min$^{-1}$. Sample air 24 from an incinerator 2 contains particles of different sizes and masses. The different masses correspond to different momentums when travelling, with the heavier particles not wanting to change direction. In Isokinetic sampling of a moving air stream, the moving sample air 24 is withdrawn from its source such that its linear velocity matches that of the sample air 24 later tested by the ICP-AES apparatus 14. Thus, isokinetic sampling ensures that at any one time representative sample air 24 is obtained by reducing the effect of the different momentum of the particles that contribute to particle size segregation.

Figure 2:
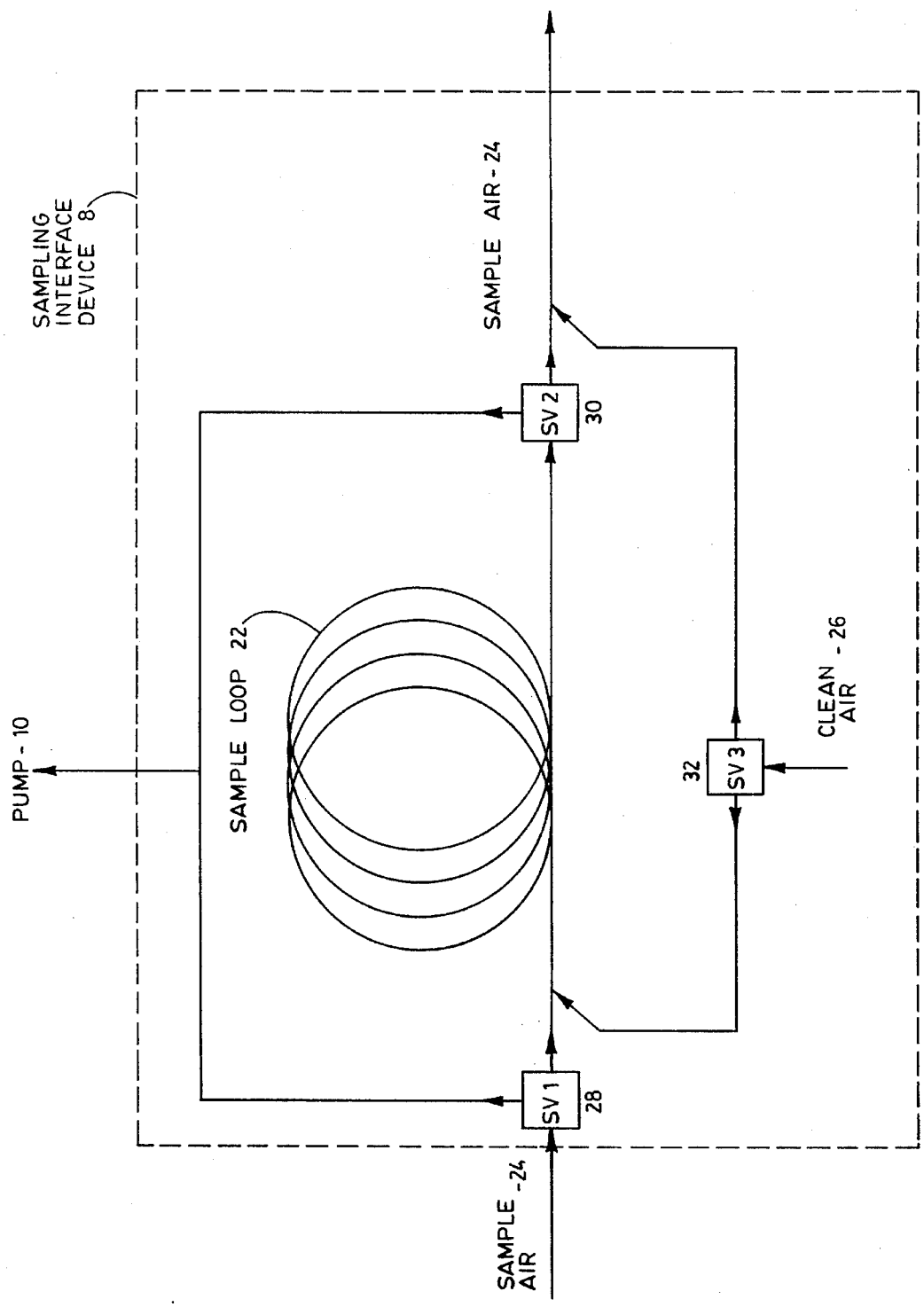
FIG. 2 illustrates the internal configuration of the sampling interface device.

Before reaching the plasma of the ICP-AES apparatus 14 the sample air 24 is introduced into the sample interface device 8. FIG. 2 is a diagram that illustrates the internal configuration of the sampling interface device 8. The operation of the sampling interface device is explained below. The device was designed to accommodate the mismatch in the relatively high sample collection flow-rates required for isokinetic sampling and the optimum flow-rates for introduction into the plasma 12.

The sampling interface device 8 has a first elongated conduit having an inlet end and an outlet end, a first solenoid valve 28 being located at the inlet end and a second solenoid valve 30 located at the outlet end. A sample loop 22, which holds a reservoir of sample air 24 is located between the first solenoid valve 28 and the second solenoid valve 30. A second elongated conduit has a first end connected to the first elongated conduit between the inlet end and the sample loop 22 to form a junction. The second conduit has a second end connected to the first conduit between the outlet end and the sample loop 22 to form a junction. A third solenoid valve 32 is located between the first end and the second end of the second conduit. The conduit can be made of any material that would not cause sample contamination, due to its being made of a metal being tested for in the sample air 24.

The plasma 12 of an ICP-AES apparatus 14 can be sustained any suitable gas, such as air or argon. Any suitable ICP-AES apparatus can be used, for example, during the field testing for airborne metals a Baird air ICP-AES apparatus was used. The ICP-AES apparatus 14, as represented by ICP 14 in FIG. 1 was powered by a 2.5 kW, 40.68 MHz radiofrequency generator and constituted the heart of the continuous emissions monitor. The air ICP-AES apparatus 14 is initiated on argon and gradually, over a period of several seconds, is converted to air operation. An automatic phase-match tuning circuit facilitates the change over from argon to air. The ICP-AES apparatus 14 is conventionally equipped with three dedicated detector modules each having light collection optics, a 74 mm monochromator with 200 µm entrance and exit slits, and a photomultiplier tube with variable voltage control.

The output of each detector is processed by a preamplifier and is then digitized using a personal computer 16. Any suitable computer can be used. In our case, a computer 16 equipped with a twelve-bit analog-to-digital converter was used. Calibrated neutral optical density filters are available to attenuate the intensity of atomic emission to within the linear range of the detection system. The ICP-AES apparatus 14 is equipped with a conventional sample introduction system including a Meinhard pneumatic nebulizer, spray chamber and peristaltic pump for liquid samples.

Sample air 24 is introduced into the plasma 12 through a sidearm in the tube connecting the spark chamber to the base of the plasma torch 12. Sample air 24 is introduced in place of, but at about the same flow-rate as the carrier gas flow used during conventional operation. The peristaltic pump and pneumatic nebulizer of the conventional ICP-AES apparatus 14, needed for testing liquid samples, are disabled or bypassed when on-line monitoring of sample air 24 is initiated. Table 1 lists the operating parameters used for instrument standardization and on-line monitoring.

TABLE 1

Air ICP-AES apparatus operating conditions for continuous emissions monitoring

| Forward power | 2.1 kW |
|---|---|
| Carrier/purge gas flow-rate | 0.8 L min$^{-1}$ |
| Plasma gas flow-rate | 2.0 L min$^{-1}$ |
| Coolant gas flow-rate | 20.0 L min$^{-1}$ |
| Aqueous sample uptake rate | 1.0 mL min$^{-1}$ |
| Detection wavelengths: | |
| Copper(I) | 324.7 nm |
| Barium(II) | 455.4 nm |
| Strontium(II) | 407.8 nm |

Sustaining an ICP-AES apparatus 14 totally on air is not a prerequisite for exciting and detecting atomic emission from airborne metals. As known in the art, any suitable gas can be used to sustain the plasma of the ICP-AES apparatus. For example, a conventional argon sustained ICP-AES apparatus, under appropriate operating conditions, can accommodate the introduction of sample air 24. To best accommodate the introduction of sample air 24 into an argon ICP-AES apparatus it is best to sustain the plasma 12 using a radiofrequency of about 40 MHz or higher, thereby achieving improved energy coupling between the radiofrequency generator and the plasma 12.

For optimum interaction between air-entrained particulates and the argon plasma into which the sample air is injected, a plasma torch with an enlarged torch injector tube, that has a 1.5 mm or greater inner diameter, is recommended. For a given gas flow rate through the injector tube a larger inner diameter will result in a reduced velocity for the entrained sample, and thus a longer residence time in the plasma.

The sampling interface device 8 of FIG. 2 has a sample loop 22 and computer-controlled three-way solenoid valves. The sample air 24 is sampled in a continuous cycle, one half of which is called sample loop filling and the other as sample loop purging. The lengths of each half of the sampling cycles and the time delay before making emission measurements are software selectable. A computer 16 controls the sampling cycle. The isokinetically sampled air flows continuously into a first valve 28 that directs the flow through the sample loop 22 to a second solenoid valve 30 that directs the flow through another conduit to the pump 10, which acts as an exhaust as well as a pump to pull the sample air 24 through the sampling interface device 8. Continuous sample flow is necessary to prevent stagnation and settling of metal analytes or pollutants in the sample line 6. During this half of the sampling cycle, clean reference air 26 from a third solenoid valve 32 is introduced into the plasma 12 at a rate of about 0.8 l min$^{-1}$ to allow for a baseline or background measurement. This half of the cycle is called sample filling.

Upon software command, as shown in FIG. 2, the computer 16 causes all three solenoid valves to switch simultaneously. The sample air 24 is diverted directly through a conduit to the pump 10 by the first solenoid valve 28. The third solenoid valve 32 directs the clean air 26, at a rate of about 0.8 l min$^{-1}$, to the upstream end of the sample loop 22 and forces the resident sample air 24 through the second solenoid valve 30 into the plasma 12 for measurement of atomic emission. The clean air 26, which can be ambient air, is pressurized, so that the sample air 24 is pushed through to the plasma 12 of the ICP-AES apparatus 14 at its optimum flow rate of about 0.8 min$^{-1}$ to 1.0 l min$^{-1}$. This half of the cycle is called sample purging.

Again, upon software command, as shown in FIG. 2, the computer 16 causes all three solenoid valves to switch back to their previous status and the sample cycle repeats. Although the duration of the cycle can be changed, the duration used in the field tests was twenty seconds for each half cycle. Emission measurements were made approximately eighteen seconds after the beginning of each half-cycle. This delay allowed sufficient time for metal pollutant or analyte concentrations in the plasma 12 to reach steady-state before the analytical measurement, and for all the metal pollutant or analyte to be removed from the plasma 12 prior to baseline or background measurement. At the end of each sampling cycle, the net emission signal for each metal pollutant being tested for is obtained by subtracting the baseline measurement from the analytical measurement.

Although "side-on" viewing of the plasma 12 is the predominant method used with an ICP-AES apparatus 14, the preferred method for detecting HAP airborne metals is achieved by axial viewing of the plasma 12. The primary advantage of axial viewing is that atomic emission can be collected from a considerably larger volume of plasma 12 and detection limits are substantially improved. The sensitivity advantage of axial viewing offsets the perturbative effects of air in the argon plasma.

A continuous emissions monitor for airborne metals requires a standardization method that is both accurate and practical for field use. Since airborne metals will be sampled and tested the ICP-AES apparatus 14 should be calibrated using metal aerosols, however, field generation of metal aerosols is neither simple nor practical. As opposed to metal aerosols, aqueous metal solutions are easily prepared in the field. An alternative to using standard metal aerosols for standardization of the ICP-AES apparatus 14 is the use of aqueous metal concentrations which can be introduced into the plasma 12 by the conventional method of nebulization. A prerequisite for using the aqueous metal solutions in place of standard metal aerosols is the prior establishment of a correlation between the metal content of aqueous solutions and the metal aerosols they are intended to simulate. For example, experiments were carried out to determine the aerosol concentration equivalent of various aqueous solution concentrations of the metals copper, barium, and strontium.

Dry aerosols of copper nitrate, barium nitrate and strontium nitrate were generated by ultrasonic nebulization of aqueous solutions of various concentrations and entrainment of the liquid aerosols through a solvent removal system. The metal content of these aerosols was determined by replicate capture of particulates on filters and later analysis of the chemically digested filters.

Figure 3:
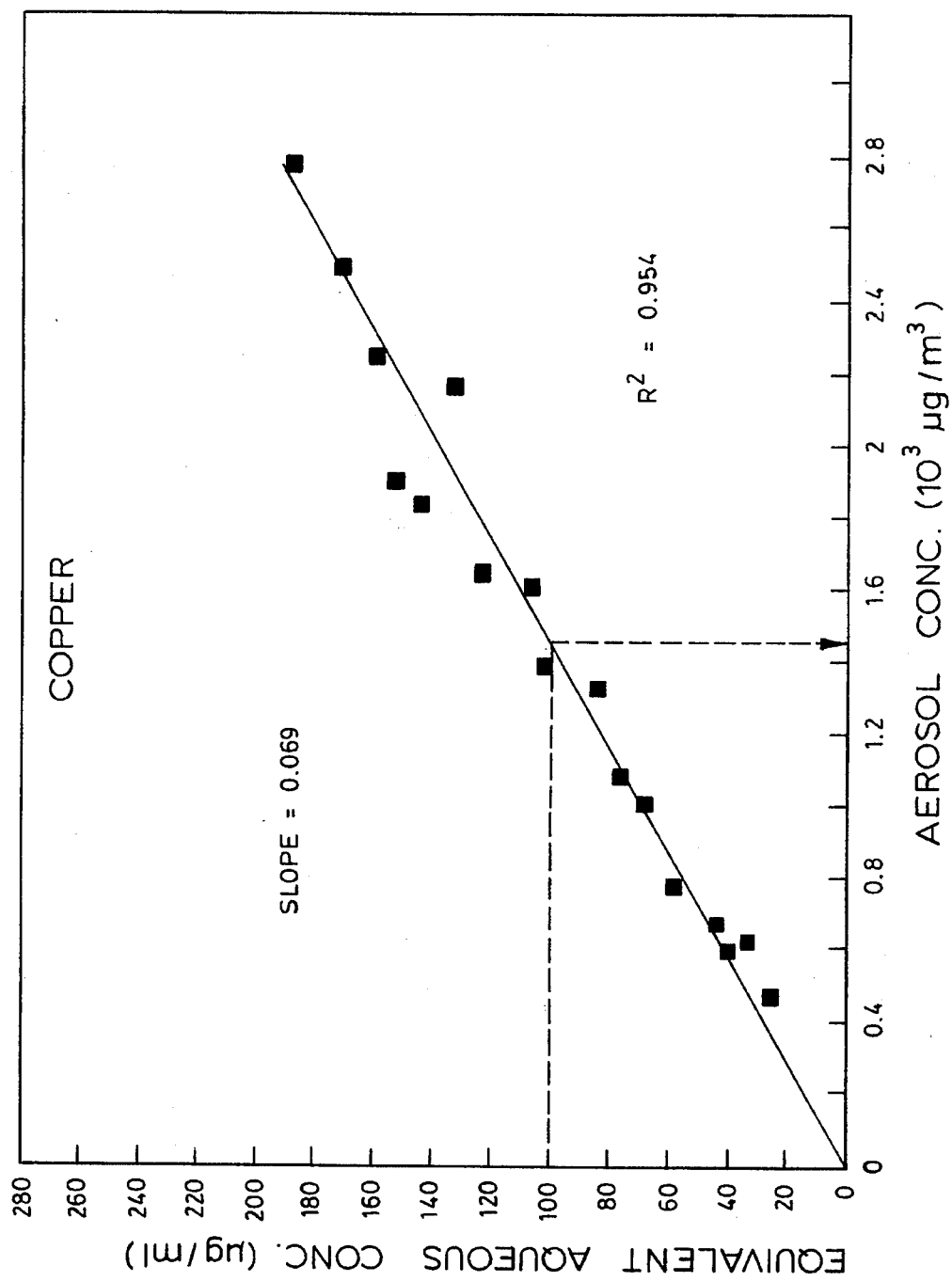
FIG. 3 is a plot of the relationship between the aqueous equivalent copper concentrations and the aerosol copper concentrations.
Figure 4:
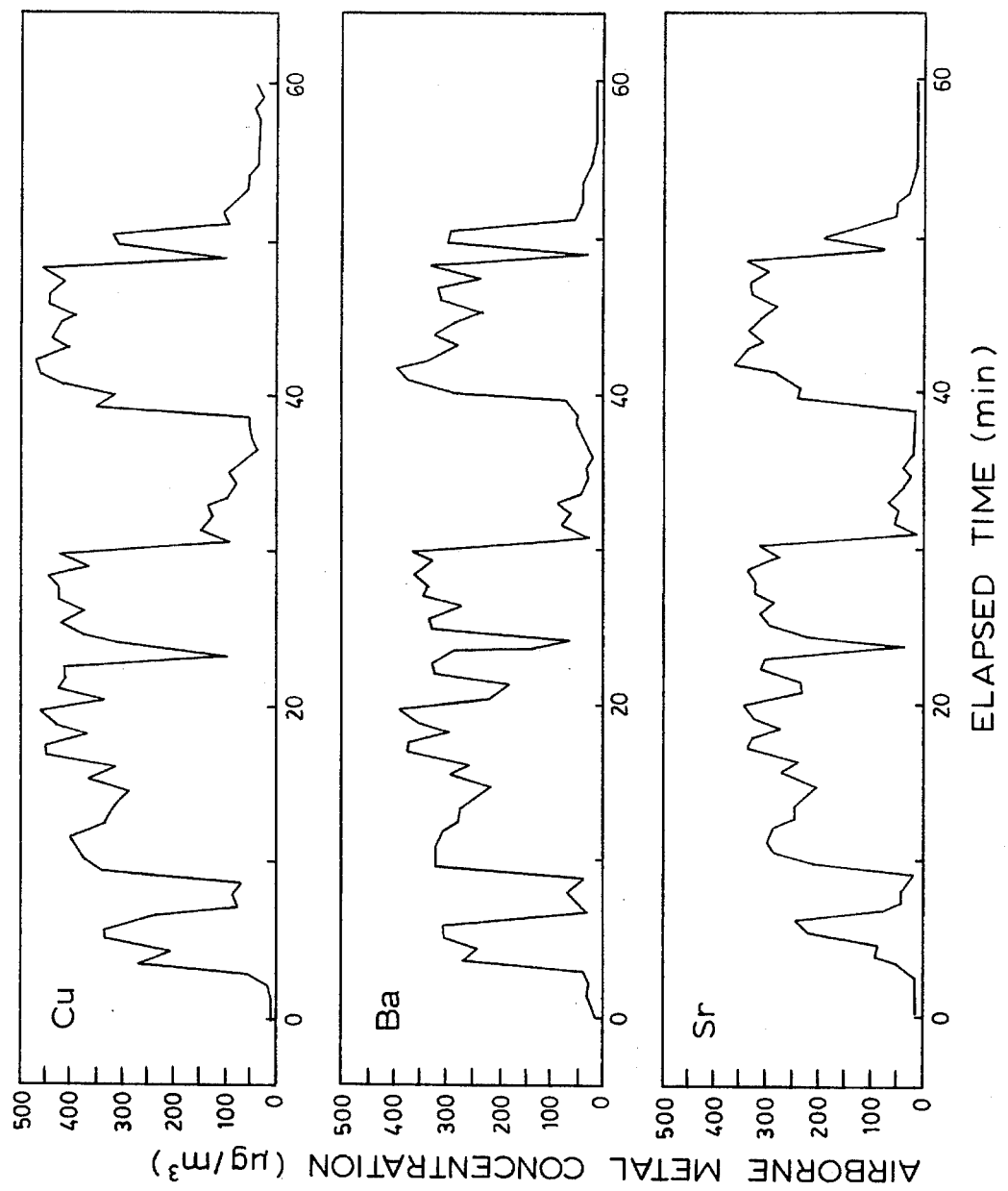
FIG. 4 is a graph of the real-time measurement of airborne copper, barium, and strontium in incinerator stack effluent showing rapid response to fluctuations in waste slurry introduction rate.
Figure 5:
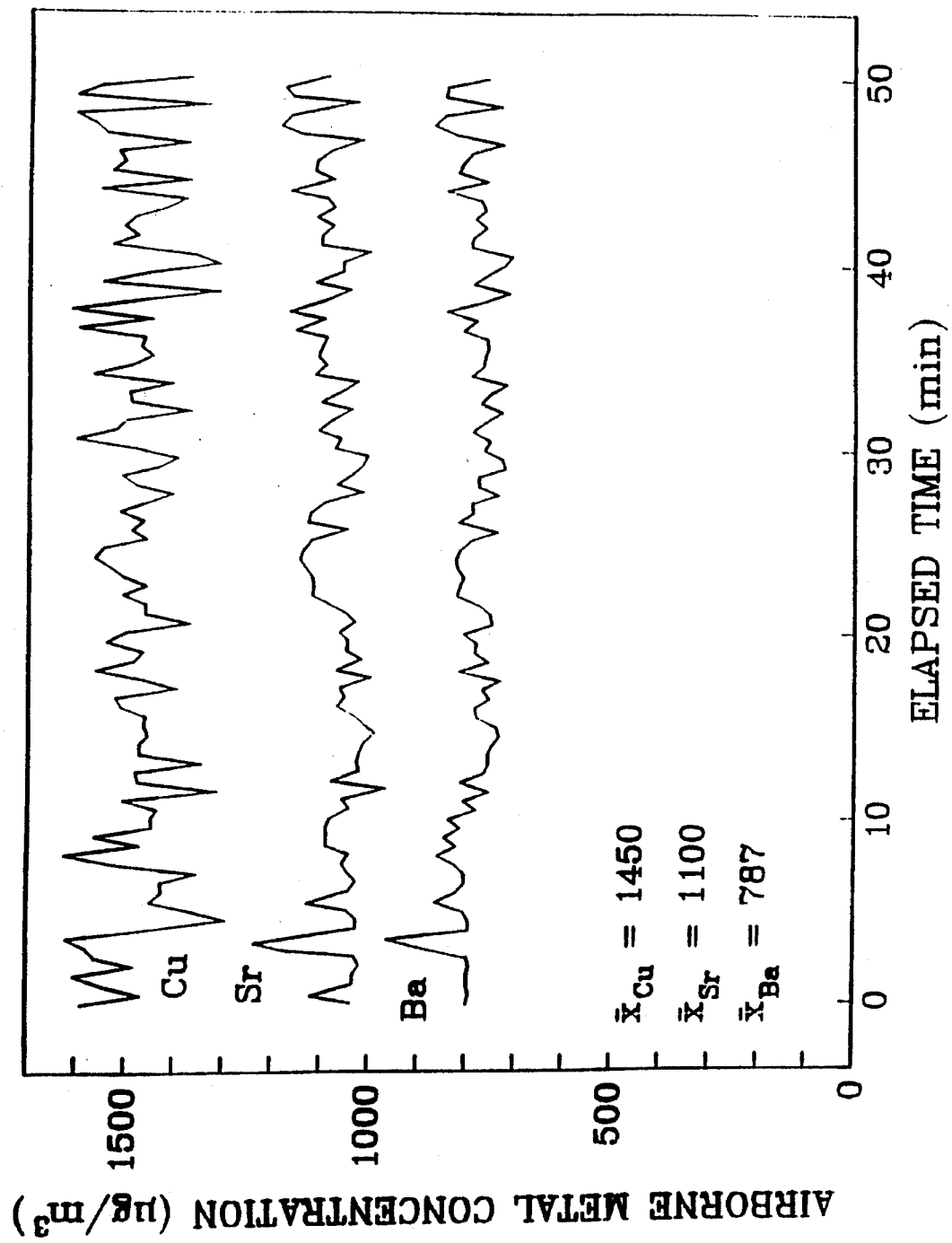
FIG. 5 is a graph of the real-time measurement of airborne copper, barium, and strontium in incinerator stack effluent. Average values of time-dependent airborne metal concentrations are shown.

Each batch of aerosol was introduced into the ICP-AES apparatus 14 to allow comparison of atomic emission intensities with those resulting from the introduction of a series of aqueous solutions of the same metals. For each batch aerosol generated, an equivalent aqueous concentration was determined. FIG. 3 is a plot of the relationship between aqueous copper equivalents and their corresponding copper nitrate aerosol concentrations. The relationship is linear and the slope of the plot indicates that, for example, a 100 µg ml$^{-1}$ aqueous copper solution is equivalent in terms of atomic emission intensity to a 1450 µg m$^{-3}$ copper aerosol. These relationships were linear over two orders of magnitude of aerosol concentration. By extrapolating to the aqueous detection limits for copper, barium and strontium of 0.025, 0.005 and 0.005 µg ml$^{-1}$, respectively, aerosol detection limits of less than 0.4 µg m$^{-3}$ can be estimated for these metals.

The laboratory determined aqueous-aerosol relationships form the basis of a field standardization scheme. Prior to continuous emissions monitoring, the ICP-AES apparatus 14 is standardized, preferably, using a series aqueous standards and a blank solution. The series of surrogate aqueous standards represent the range of aerosol concentrations expected in the sample air 24 to be monitored. Accordingly, real-time analytical measurements are converted to airborne aerosol concentrations.

A menu-driven computer 16 was used to automate all aspects of instrument operation. The aqueous solution / aerosol relationship data was determined and stored as standardization parameters. Before real-time monitoring, operating parameters were selected. A manual operation mode is available in which, for example, the solenoid valves that control the flow of the sample air 24 can be controlled manually. The computer 16 contains a microprocessor which may use a variety of inputs from various sensors, including, without limitation, sensors for atomic emission/absorption. To acquire atomic emission data, the software sends a command to an analog to digital conversion board in the computer 16 that tells it to read in signals or voltages from each of the three detectors in the conventional ICP-AES apparatus 14. These signals are then digitized and stored. Thus, initiation of monitoring, data acquisition storage, and termination of data acquisition is controlled by the computer 16. Previous standardization of the ICP-AES apparatus 14 relates the magnitude of these signals or voltages to actual atomic emission intensities and subsequently to actual metal pollutant concentrations in the sample air 24.

The following example of a preferred embodiment of the invention is provided by way of illustration and not of limitation.

EXAMPLE

The continuous emissions monitor was field tested under conditions which were intended to simulate the incineration of pyrotechnic materials. A surrogate waste slurry spiked with copper sulfate, barium nitrate and strontium nitrate was introduced into the combustion region of the incinerator. The sample air 24 was collected isokinetically through a port in the side of the stack of the incinerator 2.

Prior to continuous emission monitoring, the plasma spectrometer of the ICP-AES apparatus 14 was prepared by first igniting the plasma 12 and allowing the instrument to operate for at least one hour to ensure thermal equilibration of all optical components. After warmup, the emission detector wavelengths were optimized for maximum sensitivity. Plasma gas flow-rates were set and standardization was carried out with aqueous standard solutions of appropriate concentrations. After standardization was completed, the conventional peristaltic pump and nebulizer were disabled and the ICP-AES apparatus 14 was switched to its monitoring mode. The sampling cycle, including measurement of reference clean air 26 and sample air 24 from an incinerator 2, was repeated every 40 seconds.

During the period that real-time data shown in FIG. 4 was obtained, the rate of waste slurry introduction varied considerably due to mechanical problems with the slurry feed pump, yet this problem was detected by the present invention. Airborne copper metal concentrations varied from less than 50 μg $m^{-3}$ to about 500 μg $m^{-3}$, as shown in FIG. 4. The continuous emissions monitor of the present invention responded to changes in sample concentration and its' response was nearly instantaneous despite the time constant effect imposed by the heated 50-ft sample line 6 used to connect the sample air 24 from the incinerator 2 to the ICP-AES apparatus 14. Rapid instrument response is a prerequisite for effective process control.

To confirm the quantitative accuracy of the continuous emissions monitor, the results were compared to conventional stack monitoring using EPA Method 5. Averages of the raw, real-time data shown in FIG. 5 for copper, barium and strontium were 1450 μg $m^{-3}$, 1100 μg $m^{-3}$ and 787 μg $m^{-3}$, respectively. Time-averaged concentrations, measured using the Method 5 approach were 3260 μg $m^{-3}$, 2270 μg $m^{-3}$ and 1810 μg $m^{-3}$, respectively.

The source for the discrepancy between the real-time values and Method 5 were the 50-ft sample line used to transport the effluent to the ICP-AES apparatus. The preferred embodiment of the invention has also moved the location of the ICP-AES apparatus 14 closer to the source of sample air 24, thereby shortening the sample line 6, which minimizes the loss of metal pollutants in the sample line 6 and further improves accuracy.

Having described the preferred embodiments of this invention, it will now be apparent to one of skill in the art that other embodiments incorporating its concept may be used. It is felt, therefore, that this invention should not be limited to the disclosed embodiments, and accordingly reference should be made to the appended claims rather than the foregoing discussion of the preferred embodiments, to assess the scope of the invention.

What is claimed is:

1. A portable continuous emissions monitor for analyzing an air sample from an incinerator by an ICP-AES apparatus, comprising:

(a) a sampling interface device having:
  (i) a first elongated conduit having an inlet end and an outlet end, first solenoid valve being disposed at the inlet end and second solenoid valve being disposed at the outlet end, a sample loop being disposed between the first solenoid valve and the second solenoid valve;
  (ii) a second elongated conduit having a first end and a second end, the first end being connected to the first elongated conduit between the inlet end and the sample loop to form a junction, and the second end being connected to the first elongated conduit between the outlet end and the sample loop to form a junction, third solenoid valve being disposed between the first end and the second end;
(b) means for transporting said air sample to said sampling interface device at the inlet end of the first elongated conduit;

(c) an ICP-AES apparatus coupled to said sampling interface device at the outlet end of the first elongated conduit;

(d) means for propelling said air sample from said incinerator through said sampling interface device connected at the first solenoid valve and the second solenoid valve; and (e) an analyzer coupled to the ICP-AES apparatus, the analyzer being operable to quantify metal concentration of the air sample based on an emissions signal from the ICP-AES apparatus.

2. The monitor as claimed in claim 1 wherein said means for transporting comprises:

an isokinetic sampler having a sampling nozzle, a plurality of flow sensors and a regulated pump;

an elongated conduit connecting said isokinetic sampler with said sampling interface device; and means for heating said elongated conduit.

3. A method for feeding an air sample for analysis by an ICP-AES apparatus, comprising the step of:

(a) collecting an air sample from an incinerator to a sampling interface device;

(b) propelling the air sample continuously by a pump to the sampling interface device and to a plasma torch of an ICP-AES apparatus, the sampling interface device having a first solenoid valve to direct the air sample to a second solenoid valve to direct the air sample to exhaust, a sample loop being disposed between the first solenoid valve and the second solenoid valve;

(c) directing a low flow-rate clean air sample by a third solenoid valve into the ICP-AES apparatus to generate an emission signal;

(d) simultaneously switching said first, second, and third solenoid valves, so that said first solenoid valve directs said air sample to said pump and said third solenoid valve directs said low flow-rate clean air sample into said sample loop, so that the air sample residing in said sample loop is forced through said second solenoid valve into said ICP-AES apparatus for a measurement of atomic emission, whereby the transporting of said air sample is introduced into said ICP-AES apparatus at a low flow-rate; and (e) obtaining a net emission signal by subtracting the low flow-rate clean air sample measurement from the air sample measurement.

4. A method for feeding an air sample for analysis by an ICP-AES apparatus, as claimed in claim 3 further comprising the step of operating said ICP-AES apparatus for an appropriate period of time, so that thermal equilibration of all optical components is ensured.

5. A method for feeding an air sample for analysis by an ICP-AES apparatus, as claimed in claim 3 wherein said plasma torch of said ICP-AES apparatus is sustained on argon.

6. A method for feeding an air sample for analysis by an ICP-AES apparatus, as claimed in claim 5 wherein said ICP-AES apparatus has a radiofrequency generator that generates a radiofrequency of no less than about 40 MHz, so that an improved energy coupling between the generator and said plasma torch is achieved.

7. A method for feeding an air sample for analysis by an ICP-AES apparatus, as claimed in claim 5 wherein said plasma torch has a torch injector tube, the inner diameter of which is no less than about 1.5 mm.

8. A method for feeding an air sample for analysis by an ICP-AES apparatus, as claimed in claim 3 wherein said plasma torch is sustained on air.

9. A method for feeding an air sample for analysis by an ICP-AES apparatus, as claimed in claim 3 further comprising the step of viewing said plasma torch axially, so that atomic emission can be collected from a large volume of plasma and lower detection limits are possible.

10. A method for feeding an air sample for analysis by an ICP-AES apparatus, as claimed in claim 3 further comprising the steps of:

(a) introducing into said ICP-AES apparatus several concentrations of an aqueous metal solution to generate an atomic emission;

(b) introducing into said ICP-AES apparatus several concentrations of a metal aerosol of a same metal as said aqueous metal solution to generate an atomic emission, so that a comparison can be made of the atomic emission intensities between said aqueous metal solution and said metal aerosol and thereby creating an aqueous metal standard for said metal aerosol;

(c) standardizing said ICP-AES apparatus by introducing into it said aqueous metal standard; and (d) repeating step (c) for at least two concentrations of said aqueous metal standard, so that a metal concentration range, expected to be found in the air sample from the incinerator, is introduced into the ICP-AES.

* * * * *